United States Patent [19]
Weiser

[11] Patent Number: 4,747,684
[45] Date of Patent: May 31, 1988

[54] METHOD OF AND APPARATUS FOR REAL-TIME CRYSTALLOGRAPHIC AXIS ORIENTATION DETERMINATION

[75] Inventor: Sidney Weiser, Silver Spring, Md.

[73] Assignee: The United States of America as represented by the Secretary of the Army, Washington, D.C.

[21] Appl. No.: 89,893

[22] Filed: Aug. 27, 1987

Related U.S. Application Data

[63] Continuation-in-part of Ser. No. 913,437, Sep. 30, 1986.

[51] Int. Cl.$^4$ ..................... G01N 21/01; G01N 21/47
[52] U.S. Cl. ........................................ 356/31; 356/446
[58] Field of Search .................... 356/30, 31, 445, 446

[56] References Cited

U.S. PATENT DOCUMENTS

| | | | |
|---|---|---|---|
| 2,973,687 | 3/1961 | Pennington et al. | 356/31 |
| 3,124,638 | 3/1964 | Loro | 356/31 |
| 3,782,836 | 1/1974 | Fey et al. | 356/30 |
| 4,469,442 | 9/1984 | Reich | 356/237 |

FOREIGN PATENT DOCUMENTS

| | | | |
|---|---|---|---|
| 29266 | 6/1964 | German Democratic Rep. | 356/31 |
| 210546 | 12/1983 | Japan | 356/30 |

OTHER PUBLICATIONS

Sopori, B. L., "Optical Diffraction Technique for Determination of Crystal Orientations", *Applied Optics*, vol. 20, No. 10 (May 15, 1981), pp. 1758-1763.

*Primary Examiner*—R. A. Rosenberger
*Attorney, Agent, or Firm*—Max L. Harwell; Aubrey J. Dunn; Anthony T. Lane

[57] ABSTRACT

A specific small area of a crystal sample is scanned by a laser beam which rotates about an axis substantially perpendicular to the sample surface such that the intersection of the beam with a plane above and parallel to the surface describes a true spiral or a stepwise spiral pattern. The laser beam is reflected different amounts for different beam positions to produce a reflectance pattern indicative of crystallographic orientation.

5 Claims, 2 Drawing Sheets

METHOD OF AND APPARATUS FOR REAL-TIME CRYSTALLOGRAPHIC AXIS ORIENTATION DETERMINATION

CROSS REFERENCE TO RELATED INVENTION

This invention is a continuation-in-part of my earlier invention, disclosed in U.S. patent application Ser. No. 913,437, filed Sept. 30, 1986.

This invention described herein may be manufactured, used, and licensed by the U.S. Government for Governmental purposes without the payment of any royalties thereon.

BACKGROUND OF THE INVENTION

This invention is in the field of crystallographic axis determination methods and apparatuses. It is particularly concerned with a method and apparatus that allows such determination easily and in real time. There are various ways in which one can determine the crystallographic orientation of crystal materials. One of the oldest is probably the Laue method, in which a collimated X-ray beam is directed through a material and which produces a diffraction pattern on photographic film. Unfortunately, this method takes about 15-20 minutes to perform. Another method uses low-angle x-ray diffraction (reflection) following Bragg's Law; this method involves manual manipulations of a crystal sample to determine optimum reflectance angles, and calculation of angular deviation components. Yet another method is an optical method using a light beam reflected from an abraded or etched crystal surface. The light reflected from the surface makes a pattern on a screen; adjustment of the center of the pattern to a zero reference point gives indications of crystallographic orientation. Both of these last two methods are described in ASTM Designation: F26-84, "STANDARD METHODS FOR DETERMINING THE ORIENTATION OF A SEMICONDUCTOR SINGLE CRYSTAL." The instant invention operates in real time, requires no manual manipulations or calculations, and has a greater accuracy than the known methods.

SUMMARY OF THE INVENTION

This is a method of and apparatus for determining crystallographic orientation. The method includes the general steps of generating a laser beam and reflecting it from an essentially planar crystal surface in a substantially spiral scanned pattern and of detecting the amount of beam reflected in a particular direction as the beam scans. A pattern of reflectance is obtained from which the orientation may be determined. The apparatus includes a laser, devices for steering the laser beam such that the beam's intersection with a plane above and parallel to the crystal surface describes ; in a substantially spiral pattern, a reflective or refractive system for directing and focussing the beam onto a particular small spot on a crystal surface, a photodetector for detecting reflected beam radiation, and means for controlling the steering devices and for determining orientation from the photodetector output. By performing the orientation determination at a multiplicity of points or small spots on the crystal surface, the crystallographic orientation of the surface may be mapped.

DESCRIPTION OF PREFERRED EMBODIMENTS OF INVENTION

The method of the invention includes the steps of generating a laser beam, steering the laser beam in a substantially spiral pattern about an axis through a crystal sample, directing and focussing the beam onto a small spot on the sample in another substantially spiral pattern, detecting deflected beam radiation in a particular direction, and determining crystallographic orientation of the sample from the pattern of reflected radiation.

It might be useful to define exactly what is meant by the term "substantially spiral" in this description. Depending on whether analog or digital beam steering is employed, slightly different patterns occur. For an analog system, the laser beam is initially directed onto the spot on the sample and is continuously rotated about an axis essentially perpendicular to the surface of the sample. As the beam rotates, its angle of incidence is continuously varied, from some high initial value to a lower value or conversely. The intersection of the beam with a plane above and parallel to the crystal surface thus is a true spiral. For some angle of incidence, the reflected radiation will reach a maximum. For a digital system, the angle of incidence will be decreased or increased in stepwise small increments, such that the scan actually consists of a family of nested cones. The effect is essentially the same as if an analog change is used, if the increments are small enough; one might consider that the intersection of the beam and a plane above and parallel to the crystal surface is a step-wise spiral, but I intend the term "substantially spiral" to include it.

Figure 1:
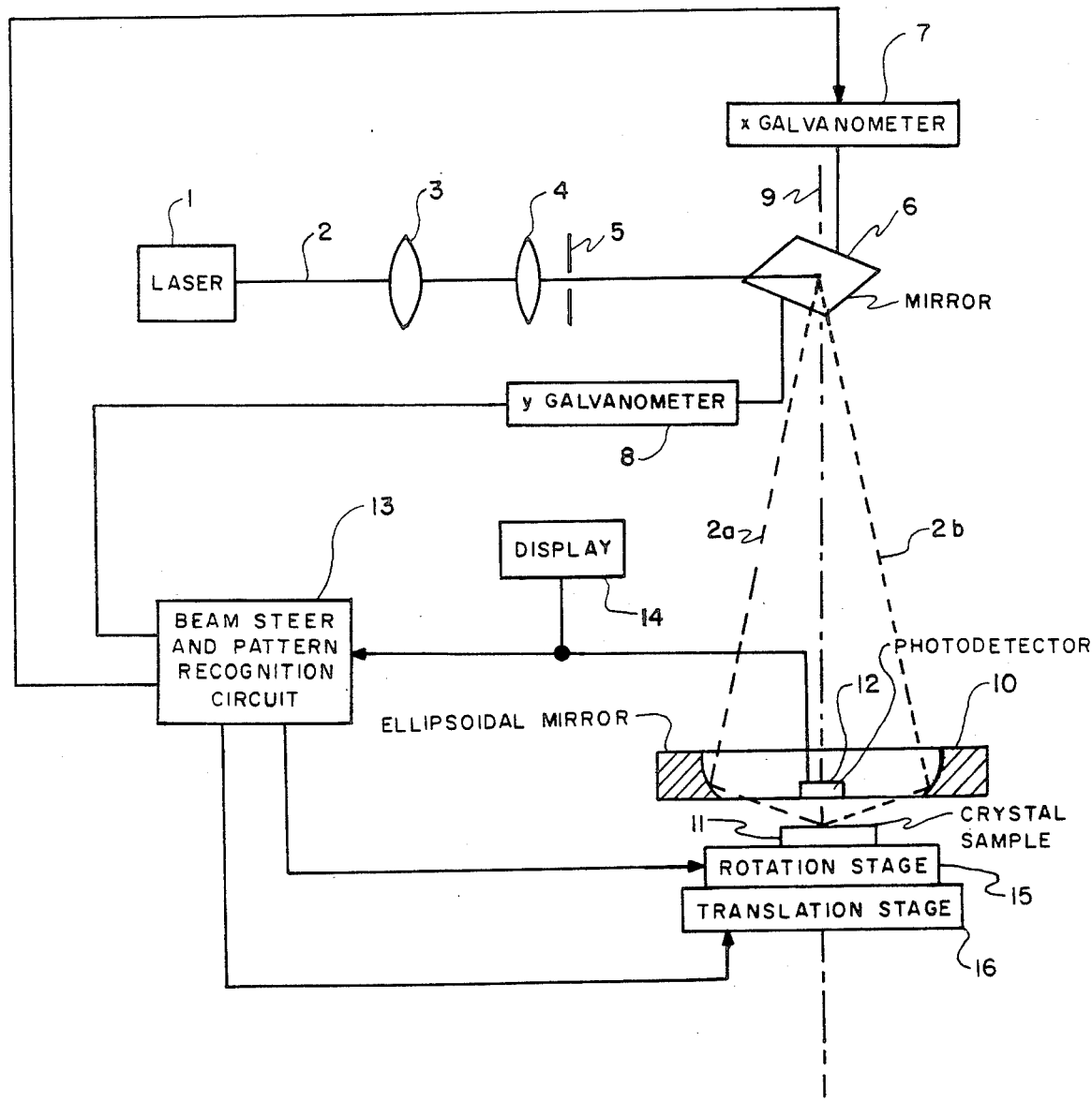
FIG. 1 is a schematic showing of the inventive apparatus.

An apparatus for performing the inventive method, as shown schematically in FIG. 1, includes laser 1 producing beam 2, primary focusing lens 3 (if needed), secondary focussing lens 4, entrance pupil 5, and mirror 6. The exit pupil 5 lens 4 is used as one focal point of an ellipsoidal optical system which will be further described below. Mirror 6 is gimballed (or equivalent) about two arbitrary orthogonal axes (x and y) and may be separately pivoted about these axes by x and y galvanometers 7 and 8. The voltages applied to the galvanometers determine the pattern the beam makes about axis 9; for 90° phase-displaced sine waves, both linearly changing in amplitude, the beam will be steered in a spiral about 9. Two positions of the steered beam are shown as 2a and 2b. The steered beam is reflected and focussed by ellipsoidal mirror 10 onto a spot on crystal sample 11. This spot is small with respect to the area of sample 11. The mirror 10 forms the other portion of the ellipsoidal optical system mentioned above, and has a focal point that is made to fall on the surface of crystal sample 11. Beam radiation reflected in a lobed pattern from 11 is detected by photodetector 12, whose output is fed to beam steer and pattern recognition circuit 13 and to a display device 14 (if desired). Crystal sample 11 may be in the form of a slab sawn from a boule, or may be a boule itself. In any event, the surface is abraded or etched to expose the characteristic surface pits and projections.

Circuit 13 consists of a clock which controls a sine or other waveform generator, whose output feeds galvanometers 7 and 8. The output of photodetector 12 is digitized in a digitizer (controlled by the clock) in 13 and feeds into a shift register configured as a ring counter and stepped by the clock. Using the information derived from the ring counter, a computer (not shown) can precisely calculate a quantative value of the angular position of the pattern lobes, in real time. These steps are synchronized with the rotation of the laser beam. Using the information derived from the ring counter, a computer (not shown) can precisely calculate a quantative value of the angular position of the pattern lobes, in real time. Pattern recognition may be done by AND gates connected to appropriate taps on the shift register. These AND gates may drive light emitting diodes to indicate the number of lobes in the reflectance pattern from the sample. Display 14 may be an oscilloscope or other such device. It will show a pattern like those shown in FIG. 2.

Figure 2:
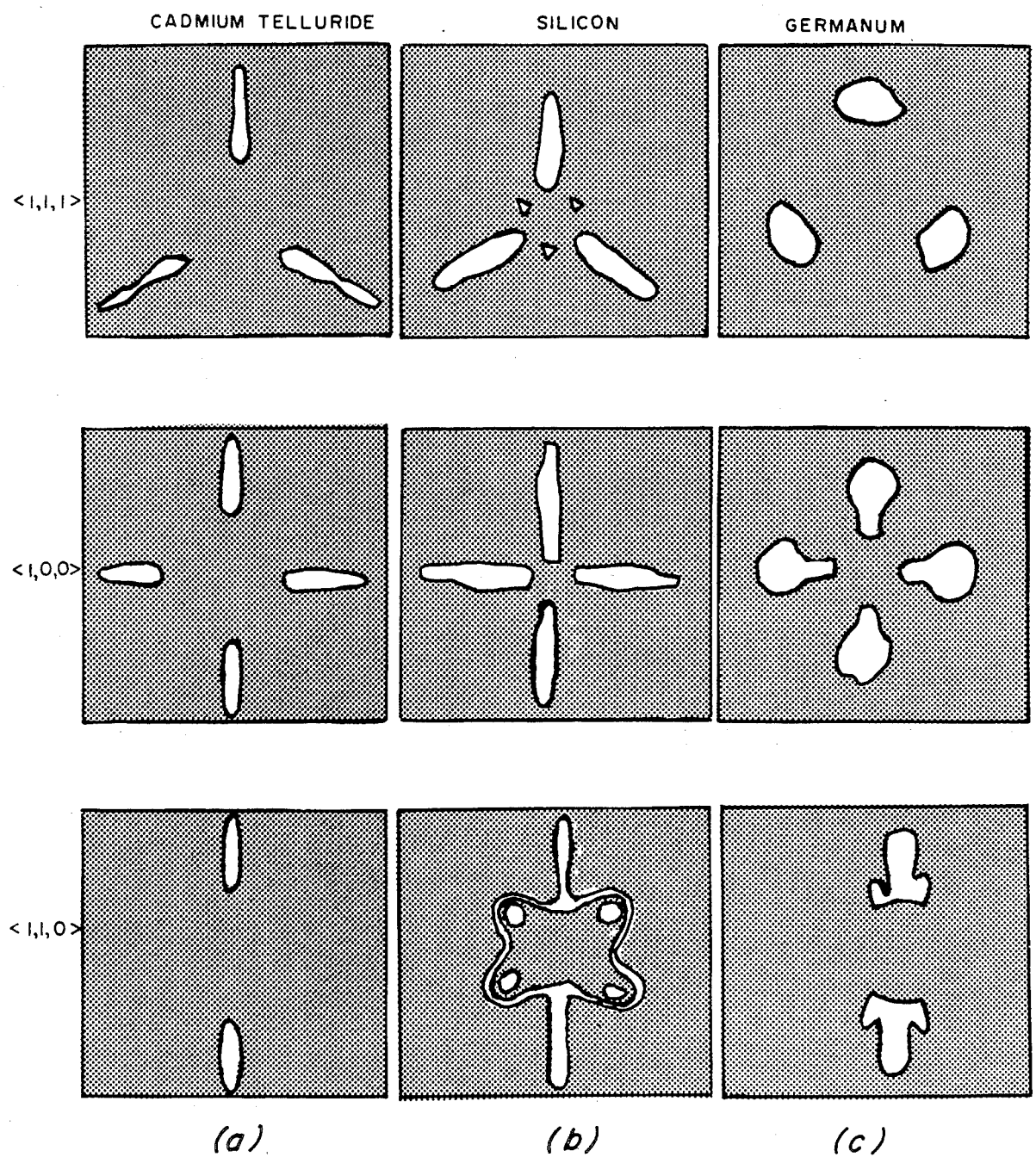
FIG. 2 shows typical reflectance patterns produced by the inventive apparatus.

As can be seen in FIG. 2, for a particular material and orientation, a lobed pattern with a particular number of lobes is produced. The direction of the lobes is indicative of the orientation direction. Columns (a), (b) and (c) respectively show $<1, 1, 1>$, $<1, 0, 0>$ and $<1, 1, 0>$ patterns for cadmium telluride, silicon, and germanium.

The instant invention has a greatly improved signal-to-noise ratio compared to the optical method described above in the BACKGROUND OF THE INVENTION. That method uses a beam essentially perpendicular to the crystal sample surface and depends upon manual manipulation of the sample and visual observation. The beam is reflected in a lobed pattern. The improved signal-to-noise ratio in this invention is achieved by using a high angle of incidence of the scanning beam. The beam is reflected from diffuse portions of the crystal surface as though such portions are specular. Such reflections, which would act as noise if detected by photodetector 12, are at angles away from 12. The scanned beam which strikes etched pits, however, is reflected toward photodetector 12. This results in a 40 db or better improvement in signal-to-noise ratio.

While specific embodiments of the invention have been taught above, other embodiments may be obvious to ones skilled in the art, in light of the teachings herein. For example, galvanometers 7 and 8 may be replaced by piezoelectric crystals or the like. Moreover, mirror 6 may be replaced by two mirrors individually driven by separate galvanometers or equivalents. Further, it may be desirable to certain cases to scan the laser beam in a pattern other than a spiral intersection of the beam with a plane above and parallel to the crystal surface; a conical toroidal, or elliptical pattern may be desirable. Moreover, circuit 13 may include a computer to control all the elements in 13 to achieve any desired scan pattern. The prototype of the invention makes use of a step-wise spiral as described above and with a beam spot size of approximately 1 mm. If desired, the beam, once the maximum reflectance angle is determined, may be continuously scanned at this angle to determine more accurately the maxima rotational positions. Further, the crystal sample may be carried by a goniometric mount also controlled by the computer. This mount may include a rotation stage 15 and a translation stage 16, or their equivalents. Obviously, additional rotation stages may be employed, if it is desired to rotate the plane of the sample about one or more axes orthogonal to axis 9. In any event, the crystal sample may be moved with respect to axis 9 such that the beam effectively moves in a step-wise raster pattern over the surface of the sample, for mapping purposes. The mapping is done by determining the crystallographic orientation of a multiplicity of small spots on the sample surface. The raster pattern may be a planar spiral, or a series of parallel lines, etc. A further application of this invention is automated crystal cuttery equipment which derives its control information from circuit 13 to cut or cleave single crystal segments of the desired orientation from a crystalline body when the body is properly oriented by the goniometric mount.

I claim:

1. A device for determining, in real time, crystallographic orientation of an essentially planar crystal sample including:

means for providing a focussed beam of coherent and essentially monochromatic electromagnetic radiation:

means for directing said beam as a spot onto a specific plane on said sample in a scanned pattern such that the intersection of said beam with a plane above and parallel to said surface is substantially spiral, wherein said spot is small with respect to the area of said sample;

means for detecting that portion of said beam reflected in a particular direction form said material, whereby the beam is reflected different amounts for different incident directions in accordance with the crystallographic orientation of the crystal material to yield a particular reflectance pattern;

and means for determining said orientation in accordance with said reflectance pattern.

2. The device as set forth in claim 1 wherein said means for providing is a laser.

3. The device as set forth in claim 1 wherein said means for directing includes means for deflecting said beam about orthogonal axes, and means for reflecting and focussing the deflected beam onto said specific place.

4. A method of determining, in real time, crystallographic orientation of an essentially planar crystal sample, including the steps of:

generating a focussed laser beam;

directing said laser beam onto a small spot on said sample;

steering said beam in a pattern about an axis essentially perpendicular to the surface of said sample such that the intersection of said beam with a plane above and parallel to said surface is substantially spiral;

detecting reflected beam radiation from said spot in a particular direction;

and determining crystallographic orientation of said sample from a pattern of reflected beam radiation as said beam is steered in said pattern.

5. A method of mapping, in real time, the planar surface of a crystal sample for crystallographic orientation by:

determining the crystallographic orientation of a multiplicity of small spots on said surface in a predetermined pattern, wherein the determination at each spot includes the steps of:

generating a focussed laser beam;

directing said beam onto a small spot on said sample, wherein said spot corresponds to one of said multiplicity of spots;

steering said beam in a pattern about an axis essentially perpendicular to the surface of said sample such that the intersection of said beam with a plane above and parallel to said surface is substantially spiral;

detecting reflected beam radiation from said spot in a particular direction;

and determining the crystallographic orientation of the spot from a pattern of reflected beam radiation as said beam is steered in said pattern.

* * * * *